United States Patent [19]

Garsky

[11] 3,940,380
[45] Feb. 24, 1976

[54] P-GLU-D-PHE-TRP-SER-TYR-2-ME.ALA-LEU-ARG-PRO-NH$_2$ AND INTERMEDIATES

[75] Inventor: Victor M. Garsky, Havertown, Pa.

[73] Assignee: American Home Products Corporation, New York, N.Y.

[22] Filed: Nov. 22, 1974

[21] Appl. No.: 526,344

[52] U.S. Cl. ................... 260/112.5 LH; 424/177
[51] Int. Cl.$^2$................ C07C 103/52; A61K 37/00
[58] Field of Search ................... 260/112.5

[56] References Cited
UNITED STATES PATENTS

| | | | |
|---|---|---|---|
| 3,824,227 | 7/1974 | Rees et al. ................... | 260/112.5 |
| 3,855,199 | 12/1974 | Foell et al. ................... | 260/112.5 |

*Primary Examiner*—Lewis Gotts
*Assistant Examiner*—Reginald J. Suyat

[57] ABSTRACT

D-Phe$^2$-2-Me.Ala$^6$-LRF, is described as well as its synthesis by solid phase techniques and novel intermediates formed by such synthesis. The novel decapeptide possess anti-ovulatory activity in mammals.

8 Claims, No Drawings

P-GLU-D-PHE-TRP-SER-TYR-2-ME.ALA-LEU-ARG-PRO-NH₂ AND INTERMEDIATES

This invention relates to the novel decapeptide p-Glu-D-Phe-Trp-Ser-Tyr-2-Me·Ala-Leu-Arg-Pro-Gly-NH₂, its process of manufacture and novel intermediates formed in such synthesis.

The luteinizing hormone releasing factor (hereafter called LRF) is the decapeptide, L-(5-oxoprolyl)-L-histidyl-L-tryptophyl-L-seryl-L-tyrosyl-glycyl-L-leucyl-L-arginyl-L-prolylglycineamide. This decapeptide is secreted by the hypothalamus and carried to the adenohypophysis where it stimulates the release of the luteinizing hormone and the follicle stimulating hormone. In (i) copending application Ser. No. 402,958 filed Oct. 3, 1973, now U.S. Pat. No. 3,855,199, D-Phe²-D-Ala⁶-LRF is described and claimed as having antiovulatory activity; (ii) copending application Ser. No. 417,983 filed Nov. 21, 1973, now U.S. Pat. No. 3,886,137, D-Phe²-D-Leu⁶ is described and claimed as having antiovulatory activity and (iii) copending application Ser. No. 459,513 filed Apr. 10, 1974, now U.S. Pat. No. 3,886,135, D-Phe²-D-Pgl⁶-LRF is described and claimed as having anti-ovulatory activity. U.S. Pat. No. 3,824,227 describes D-Phe²-LRF as an antagonist of LRF in vitro. Other modifications of LRF are described by Fujino et al., Biochemical and Biophysical Research Communications, 49, No. 3 pp 698–705 (Nov. 1972).

The present invention concerns itself with further structural modifications of LRF which exhibit anti-ovulatory activity.

The novel peptides of the present invention are represented by the compounds of the formula:

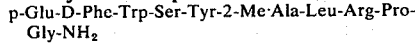

and its non-toxic salts. All chiral amino acid residues identified in formula I supra, and the other formulas hereinafter are of the natural or L-configuration unless specified otherwise. In formula I and the other formulas herein "2-Me·Ala" means "2-methylalanyl". Another identification for 2-Me·Ala is "C-Me-Ala".

Also contemplated within the scope of the present invention are intermediates of the formula

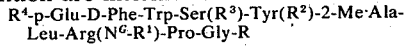

wherein:
R is selected from the class consisting of NH₂, OH, O-(lower)alkyl, in which (lower)alkyl is C₁ through C₆ (e.g. methyl, ethyl, pentyl, hexyl, etc.) and O-benzyl;

N^G means the side chain nitrogen atoms of arginine;

R¹ is a protecting group for the N^δ, N^ω and N^ω' nitrogen atoms of arginine selected from the class consisting of nitro, tosyl, benzyloxycarbonyl, adamantyloxycarbonyl and tert-butyloxycarbonyl; or R¹ is hydrogen which means there are no protecting groups on the side chain nitrogen atoms of arginine. Where the protecting group is nitro or tosyl, the protection is on either one of the N^ω, N^ω' nitrogens and in the case of benzyloxycarbonyl, or adamantyloxycarbonyl, the protection is on the N^δ nitrogen and either one of the N^ω, N^ω' nitrogen atoms. The preferred protecting group defined by R¹ is tosyl;

R² is a protecting group for the phenolic hydroxyl group of tyrosine selected from the class consisting of tetrahydropyranyl, tert-butyl, trityl, benzyl, 2,6-dichlorobenzyl, benzyloxycarbonyl and 4-bromobenzyloxycarbonyl. The preferred protecting group is benzyl; or R² is hydrogen which means there is no protecting group on the phenolic hydroxy function;

R³ is a protecting group for the alcoholic hydroxyl group of serine and is selected from the class consisting of acetyl, benzoyl, tetrahydropyranyl, tert-butyl, trityl, benzyl, 2,6-dichlorobenzyl, benzyloxycarbonyl or R³ is hydrogen which means there is no protecting group on the alcoholic oxygen atom. Preferably R³ is benzyl;

R⁴ is preferably hydrogen or an α-amino protecting group. The α-amino protecting group contemplated by R⁴ are those known to be useful in the art in the step-wise synthesis of polypeptides. Among the classes of α-amino protecting groups covered by R⁴ are (1) acyl type protecting groups illustrated by the following: formyl, trifluoroacetyl, phthalyl, toluenesulfonyl (tosyl), benzenesulfonyl, nitrophenylsulfenyl, tritylsulfenyl, o-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R⁴ are selected from the class consisting of tert-butyloxycarbonyl, cyclopentyloxycarbonyl, tert-amyloxycarbonyl and d-isobornyloxycarbonyl.

In formula II at least one of R¹, R² or R³ is a protecting group.

A further aspect of the present invention relates to intermediates linked to a solid resin support. These intermediates are represented by the formula:

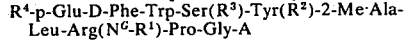

wherein:
R¹, R², R³ and R⁴ have the same meaning as in Formula II;

"A" is an anchoring bond used in solid phase synthesis linked to a solid resin support. "A" is selected from the class consisting of:

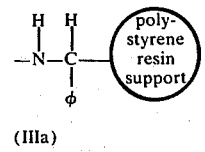

(IIIa)

and

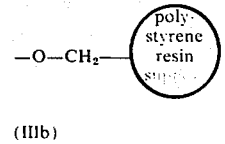

(IIIb)

The symbol φ means "phenyl". The polystyrene resin support is preferably a copolymer of styrene with about 1 to 2% divinyl benzene as a cross linking agent which causes the polystyrene polymer to be completely insoluble in most organic solvents. The polystyrene polymer is composed of long alkyl chains bearing a phenyl ring on every second carbon and the terminal amino acid residue (Gly) is joined through a covalent carbon to nitrogen or oxygen bond to these phenyl rings. The alkyl chains are cross linked at approximately every fiftieth carbon by p-substituted phenyl residues derived from divinyl benzene.

In selecting a particular side chain protecting group to be used in the synthesis of the peptides of formula (I), the following rules should be followed: (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

Illustrative of pharmaceutically acceptable non-toxic salts of formula I are hydrochloride, hydrobromide, sulfate, phosphate, maleate, acetate, citrate, benzoate, succinate, malate, ascorbate, and the like.

The peptides of formula (I) through (III) are prepared using solid phase synthesis. The synthesis is commenced from the C-terminal end of the peptide using an α-amino protected resin. Such a starting material can be prepared by attaching an α-amino protecting glycine to a benzhydrilamine resin, a chloromethylated resin or a hydroxymethyl resin, the former being preferred. The preparation of a benzhydrilamine resin is described by P. Rivaille et al., Helv. 54, 2772 (1971) and the preparation of the hydroxymethyl resin is described by Bodanszky et al., Chem. Ind (London) 38, 1597–98 (1966). A chloromethylated resin is commercially available from Bio Rad Laboratories Richmond, California and the preparation of such a resin is described by Stewart et al., "Solid Phase Peptide Synthesis" (Freeman & Co. San Francisco 1969), Chapter 1, pp 1–6. In using the benzhydrilamine resin an amide anchoring bond is formed with the α-amino protected glycine as follows:

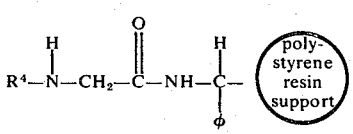

This permits the C-terminal amide function to be obtained directly after the amino acid sequence in the synthesis is complete by cleaving off the resin support to form the glycine amide at the C-terminal portion of the desired peptide of formula (I). When the other resins are used, the anchoring bond is the benzylester group as defined supra in Formula (IIIb), which after cleavage of the peptide from the resin support must be converted to the C-terminal amide. The preferred procedure is to ammonolyse the protected peptide off the resin and then remove the protecting group by hydrogenolysis or by hydrogen fluoride cleavage. An alternate procedure would be to cleave by transesterification with methanol/(Et)$_3$N and then convert the resulting ester into an amide and subsequently deprotect as described above. See J. M. Stewart "Solid Phase Peptide Synthesis", pp 42–46 (W. H. Freeman & Co. 1968).

The α-amino protected glycine is coupled to the benzhydrilamine resin with the aid of a carboxyl group activating compound such as dicyclohexylcarbodiimide. Following the coupling of the α-amino protected glycine to the resin support, the α-amino protecting group is removed such as by using trifluoroacetic acid in methylene chloride, trifluoroacetic acid alone or HCl in dioxane. The deprotection is carried out at a temperature between about 0°C and room temperature. Other standard cleaving reagents and conditions for removal of specific α-amino protecting groups may be used as described in Schroder & Lubke, "The Peptides", 1 72–75 (Academic Press 1965). After removal of the α-amino protecting group the remaining α-amino protected amino acids are coupled step-wise in the desired order to obtain a compound of formula (I). However, as an alternate to adding each amino acid separately to the reaction, some of them may be coupled prior to addition to the solid phase reactor. If the C-terminal end of the peptide unit is represented by glycine or proline and the coupling is carried out with DCC, a minimum of racemization is encountered with proline and no problems are encountered with glycine which has no asymmetric centre. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence has been synthesized, the peptide is removed from the resin support by treatment with a reagent such as hydrogen fluoride which not only cleaves the peptide from the resin but also cleaves all remaining side chain protecting groups and the α-amino protecting group (if present) on pyroglutamic acid to obtain directly a compound of formula I in the case where the benzhydrilamine resin was used. Where a chloromethylated resin is used the peptide may be separated from the resin by methanolysis after which the recovered product is chromatographed on silica gel and the collected fraction subject to ammonolysis to convert the methyl ester to the C-terminal amide. Any side chain protecting group may then be cleaved as previously described or by other procedures such as catalytic reduction (e.g. Pd on C) using conditions which will keep the Trp moiety intact. When using hydrogen fluoride for cleaving, anisole is included in the reaction vessel to prevent the oxidation of labile amino acid (e.g. tryptophan).

The solid phase synthesis procedure discussed supra is well known in the art and has been essentially described by M. Monahan et al., C. R. Acad. Sci. Paris, 273 508 (1971).

The nomenclature used for peptides is described by Schroder & Lubke, supra, pp viii–xxix and in Biochemistry 11, 1726–1732 (1972).

The following examples are illustrative of the preparation of the compounds of formulas I through III.

EXAMPLE 1

L-(5-oxoprolyl)-D-phenylalanyl-L-tryptophyl-O-benzyl-L-seryl-O-2,6-dichlorobenzyl-L-tyrosyl-2-methylalanyl-L-leucyl-$N^g$-tosyl-L-arginyl-L-prolyl-glycyl benzhydrylamine resin Benzhydrylamine hydrochloride resin (10.0 g, 5.3 m moles) is placed in a Beckman 990 peptide synthesizer reaction vessel and treated in the following manner:
1. methylene chloride (three times);
2. 5 minutes prewash with 1:1 trifluoroacetic acid-methylene chloride (v/v) containing 0.5% dithioerythritol;
3. 30 minute deprotection with the above described trifluoroacetic acid;
4. methylene chloride (six times);
5. 15% triethylamine in dimethylformamide (three times);
6. methylene chloride (six times).

A contact time of 1.5 minutes is allowed for each wash unless otherwise indicated.

The resin is gently stirred with t-butyloxycarbonyl glycine (5.6 g, 31.8 m moles in methylene chloride) and 35.0 ml of 1 M diisopropylcarbodiimide (DIC) in methylene chloride (DIC added in two portions over 30 minutes). After stirring for 18 hours the peptide-resin is washed successively with methylene chloride (three times), dimethylformamide (three times) and methylene chloride (three times). Any unreacted sites are acylated with acetylimidazole (60 ml, 2.5% in methylene chloride) for 30 minutes and the resin washed with methylene chloride (six times).

The deprotection of the attached amino acid is carried out as described in steps (1) through (6) above.

The following amino acid residues are then introduced consecutively: t-Boc-L-proline (6.8 g, 31.8 m moles in methylene chloride, 35 m moles DIC), t-Boc-L-$N^g$-tosyl-L-arginine (11.2 g, 31.8 m moles in methylene chloride, 35 m moles DIC), t-Boc-$\alpha$-aminoisobutyric acid (6.3 g, 31.8 m moles in methylene chloride, 35 m moles DIC), t-Boc-O-2,6-dichlorobenzyl-L-tyrosine (15.0 g, 31.8 m moles in dimethylformamide, 35 m moles DIC), t-Boc-O-benzyl-L-serine (9.4 g, 31.8 m moles in methylene chloride, 35 m moles DIC), t-Boc-L-tryptophan (9.7 g. 31.8 m moles in dimethylformamide, 35 m moles DIC). Reaction time for each coupling is three hours. Following each coupling the peptide-resin is washed and acylated as described above. Removal of the $\alpha$-amino protecting group at each step is performed as described for the deprotection of the t-Boc-glycine-resin (steps 1-6). The washed octapeptide-resin is dried, weighed (16.6 g) and the synthesis continued with 62% (10.3 g, 3.3 m moles) of the peptide-resin. The next amino acid added is t-Boc-D-phenylalanine (5.3 g, 20 m moles in methylene chloride, 22 m moles DIC) followed by L-2-pyrrolidone-5-carboxylic acid (2.6 g, 20 m moles in dimethylformamide, 22 m moles DIC). The washed decapeptide resin is dried in vacuo to yield 12.1 g of the above-titled product.

EXAMPLE 2

L-(5-oxoprolyl)-D-phenylalanyl-L-tryptophyl-L-seryl-L-tyrosyl-2-methylalanyl-L-leucyl-L-arginyl-L-prolyl-glycinamide acetate salt Removal of the protecting groups and cleavage of the decapeptide from the resin is accomplished by treating 12 g, of the dried peptide-resin of Example 1 in vacuo with anhydrous liquid hydrogen fluoride (100 ml) and anisole (25 ml) at 0° for 45 minutes. The hydrogen fluoride and anisole are removed under reduced pressure and the residue suspended in 50% acetic acid. After filtration the filtrate is extracted with hexane and the aqueous phase lyophilyzed to leave the above-titled product (2.0 g).

EXAMPLE 3

Purification and characterization of L-(5-oxoprolyl)-D-phenylalanyl-L-tryptophyl-L-seryl-L-tyrosyl-2-methylalanyl-L-leucyl-L-arginyl-L-prolyl-glycinamide acetate salt The above-titled crude product is purified as follows: 2.0 g of this product is dissolved in a minimum amount of 50% acetic acid and applied to a column (2.9 × 100 cm) of Sephadex G-15 medium in 50% acetic acid. The fractions are monitored by the Folin-Lowry method. The column is eluted with 50% acetic acid and 3.9 ml fractions collected. Tubes 115–132 are shown to be homogenous by thin layer chromatography systems 4 : 1 : 5 (n-butanol : acetic acid : water) $R_f$ 0.45, and 7 : 7 : 6 (isoamyl alcohol : pyridine : water) $R_f$ 0.81, on silica gel G. Thin layer chromatograms are visualized with iodine and chlorine peptide reagent.

After hydrolysis of the peptide (6 N HCl, 4% thioglycolic acid) for 20 hours at 110°C in a closed system under nitrogen, the following values for the product are obtained: Glu 0.94, Phe 1.05, Trp 0.83, Ser 0.64, Tyr 0.99, 2-Me-Ala 0.88, Leu 0.93, Arg 0.98, Pro 1.01, Gly 1.00.

The compounds of formula I possess anti-ovulatory activity and hence are potentially useful in inhibiting fertility in female mammals. In tests conducted with female rats (225 to 250 grams body weight) complete ovulation inhibition was achieved in all of the rats tested at a dose of about 24 mg/kg. The test was conducted with mature Sprague-Dawley rats, normally cycling unanesthetized, proestrous rats. On the afternoon of proestrous, each rat in the test group received six subcutaneous injections of the acetate salt of formula I in corn oil, each injection being given a half hour following the previous injection. The rats are sacrificed the next morning and the number of animals ovulating and the number of ova shed are recorded following the procedure described by E. S. France, Neuroendocrinology 6, pp 77–89 (1970). The absence of or a significant decrease in the number of ova is the criterion for an anti-ovulation effect. At a dose of 1 mg per injection inhibition of ovulation was achieved in all of the rats tested.

The compounds of formula I can be administered to mammals intravenously, subcutaneously, intramuscularly or orally for fertility inhibition and control. The effective dosage will vary with the form of administration and the particular species of mammal to be treated. A typical dosage is a physiological saline solution containing a compound of formula I administered in a dose range of between about 20 to 30 mg/kg of body weight. Oral administration may be in either solid or liquid form.

What is claimed is:

1. A compound selected from the group consisting of
L-p-Glu-D-Phe-L-Trp-L-Ser-L-Tyr-2-Me-Ala-L-Leu-L-Arg-L-Pro-Gly-NH₂
and
R⁴-L-p-Glu-D-Phe-L-Trp-L-Ser(R³)-L-Tyr(R²)-2-Me-Ala-L-Leu-L-Arg(N^G-R¹)-L-Pro-Gly-R
and its non-toxic salts; wherein R is selected from the class consisting of NH₂, OH, O-(lower)alkyl and O-benzyl; R¹ is selected from the class consisting of hydrogen and a protecting group for the N$^\delta$, N$^\omega$ and N$^{\omega'}$ nitrogen atoms of arginine selected from nitro, tosyl, benzyloxycarbonyl and adamantyloxycarbonyl;

R² is selected from the class consisting of hydrogen and a protecting group for the phenolic hydroxyl group of tyrosine selected from tert-butyl, tetrahydropyranyl, trityl, benzyl, 2,6-dichlorobenzyl, benzyloxycarbonyl and 4-bromobenzyloxycarbonyl;

R³ is selected from the class consisting of hydrogen and a protecting group for the alcoholic hydroxyl group of serine and is selected from acetyl, benzoyl, tetrahydropyranyl, tert-butyl, trityl, 2,6-dichlorobenzyl, benzyl and benzyloxycarbonyl;

R⁴ is selected from the class consisting of hydrogen and an α-amino protecting group, with the proviso that at least one of R¹, R² and R³ is a protecting group.

2. A compound according to claim 1 wherein R is NH₂.

3. A compound according to claim 1 wherein R is NH₂, R¹ is tosyl, R² is 2,6-dichlorobenzyl, R³ is benzyl and R⁴ is hydrogen.

4. A compound according to claim 1 which is selected from: L-Pyroglutamyl-D-phenylalanyl-L-tryptophyl-L-seryl-L-tyrosyl-2-methylalanyl-L-leucyl-L-arginyl-L-prolylglycinamide and its nontoxic acid addition salts.

5. A compound of the formula:
R⁴-L-p-Glu-D-Phe-L-Trp-L-Ser(R³)-L-Tyr(R²)-2-Me-Ala-L-Leu-L-Arg-(N^G-R¹)-L-Pro-Gly-A
wherein:

R¹ is selected from the class consisting of hydrogen and a protecting group for the N$^\delta$, N$^\omega$ and N$^{\omega'}$ nitrogen atoms of arginine selected from nitro, tosyl, benzyloxycarbonyl and adamantyloxycarbonyl;

R² is selected from the class consisting of hydrogen and a protecting group for the phenolic hydroxyl group of tyrosine selected from tert-butyl, tetrahydropyranyl, trityl, benzyl, 2,6-dichlorobenzyl, benzyloxycarbonyl and 4-bromobenzyloxycarbonyl;

R³ is selected from the class consisting of hydrogen and a protecting group for the alcoholic hydroxyl group of serine and is selected from acetyl, benzoyl, tetrahydropyranyl, tert-butyl, trityl, 2,6-dichlorobenzyl, benzyl and benzyloxycarbonyl;

R⁴ is selected from the class consisting of hydrogen and an α-amino protecting group; and A is selected from the class consisting of

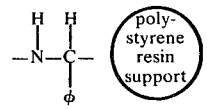

and

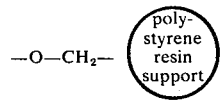

wherein said polystyrene resin is cross linked through the phenyl group on each second carbon atom of the alkyl chain of said polystyrene.

6. A compound according to claim 5 wherein R⁴ is an α-amino protecting group which is selected from the class consisting of tert-butyloxycarbonyl, cyclopentyloxycarbonyl, tert-amyloxycarbonyl and isobornyloxycarbonyl.

7. A compound according to claim 5 wherein A is a benzhydrilamine resin and R⁴ is hydrogen.

8. A compound according to claim 7 wherein R¹ is tosyl, R² is 2,6-dichlorobenzyl and R³ is benzyl.

* * * * *